(12) United States Patent
Mackey et al.

(10) Patent No.: US 6,589,050 B1
(45) Date of Patent: Jul. 8, 2003

(54) FRAGRANCED ORTHODONTIC APPLIANCES AND METHOD OF FORMING SAME

(76) Inventors: Paul W. Mackey, 13 A Avenue de Terveuren, B-1040 Brussels (BE); Tanya L. Woods, 1013 E. Third St., Royal Oak, MI (US) 48067

( * ) Notice: Subject to any disclaimer, the term of this patent is extended or adjusted under 35 U.S.C. 154(b) by 0 days.

(21) Appl. No.: 09/806,987
(22) PCT Filed: Oct. 20, 1999
(86) PCT No.: PCT/US99/24631
§ 371 (c)(1), (2), (4) Date: May 29, 2001
(87) PCT Pub. No.: WO00/23001
PCT Pub. Date: Apr. 27, 2000

Related U.S. Application Data

(60) Provisional application No. 60/105,133, filed on Oct. 21, 1998.

(51) Int. Cl.⁷ .................................................. A61C 7/00
(52) U.S. Cl. ................................................. 433/2; 433/6
(58) Field of Search ........................ 433/2, 5, 6; 264/16

(56) References Cited

U.S. PATENT DOCUMENTS

| 3,567,118 A | * | 3/1971 | Shepherd et al. ............... 239/6 |
| 3,808,686 A |   | 5/1974 | Tauman et al. ................... 32/2 |
| 3,941,858 A | * | 3/1976 | Shepherd et al. ........... 260/885 |
| 4,946,901 A | * | 8/1990 | Lechner et al. ............. 525/305 |
| 5,080,583 A |   | 1/1992 | Hunting ......................... 433/2 |

* cited by examiner

*Primary Examiner*—Kevin Shaver
*Assistant Examiner*—Melba Bumgarner
(74) *Attorney, Agent, or Firm*—Howard & Howard

(57) ABSTRACT

The fragrant orthodontic appliance, the method of forming the same include mixing a powdered polymeric component, a liquid monomeric component, applying the components to a mold, and cold curing the orthodontic appliance. Both the powdered and the liquid components contain a selected fragrant oil. Suspension polymerization process is utilized to encapsulate the fragrance in the powdered polymeric component.

7 Claims, No Drawings

FRAGRANCED ORTHODONTIC APPLIANCES AND METHOD OF FORMING SAME

This application claims the benefit of provisional application Ser. No. 60/105,133, filed Oct. 21, 1998.

BACKGROUND OF THE INVENTION

This invention relates to fragranced orthodontic appliances and particularly flavored or fragranced orthodontic appliances having encapsulated fragranced oils encapsulated and distributed throughout the matrix of the polymeric appliance. Orthodontic appliances are employed in the practice of correction or prevention of irregularities of the teeth or structure of the oral cavity. These appliances are custom made to conform to the upper and lower palate of the mouth and typically consist of a hard acrylic resin in which wires or auxiliary devices can optionally be embedded. Some such appliances are Frankel, Bionator, Bite Splint, Retainer, Sagittal, and Bonded Palatal Expander, etc. These appliances are unlike other dental prosthesis in that they are custom made with what is commonly known in the art as "cold cure" acrylic.

"Cold cure" acrylic is made up of two components: a polymeric component and a monomeric component. To produce the desired acrylic material, the polymer is used as the powdered compound and the monomer is used as the liquid compound. These materials are prepared in a away that when mixed a free radical polymerization of the monomeric liquid occurs at room temperature which results in a solid homogeneous acrylic material. Typically, the polymer and monomer are comprised of an ester of acrylic or methacrylic acid with methyl methacrylate liquid and poly (methyl methacrylate) powder being, the orthodontic appliance industry standard material. Other esters such as ethyl methacrylate have been used but are not in wide spread use in methyl methacrylate.

Orthodontic appliances are commonly used as part of a regimented treatment program and habitual wearing of the appliance is required to achieve the desired result. Anyone who has had orthodontic treatment is aware of the discomfort associated with the wearing of an orthodontic appliance such as Retainer. They are bulky and often impeded clear speech. Exposed wires can also be an embarrassment, especially to younger people. As a result of these discomforts patient compliance in wearing these appliances is less than ideal.

In order to improve patient compliance with the use of these appliances the concept of flavoring or fragrancing the appliance has been applied. For example, U.S. Pat. No. 5,080,583 discloses the use of fragrancing or flavoring oil in the liquid monomeric component of the "cold cure" acrylic resin thereby achieving a flavored or fragranced appliance. U.S. Pat. No. 3,808,686 discloses the use of a scented surface coating applied as a solution onto the prepared acrylic device. These approaches have proven disadvantageous as they provide a relatively short-lived flavor or fragrance, i.e., typically 2 to 3 days in the case of U.S. Pat. No. 5,080,583 and, only minutes in the case of the surface coating. It can be speculated that simply increasing the quantity of flavor or fragrancing oil in the case of U.S. Pat. No. 5,080,583 could increase the duration of the flavor or fragrance. This has also proved disadvantageous because the inventor found that cold cure was inhibited. Thus there is a limit to the total quantity of flavor or fragrance that the appliance can contain. The prior art also discloses the inclusion of a flavor-releasing capsule in the acrylic base member designed to release flavor over long periods. However, this approach has also proved disadvantageous because the appliance is required to be of suitable thickness to accommodate the capsule and most appliances such as those listed are simply too thin.

SUMMARY OF THE INVENTION

Clearly there is a need to develop a technology for fragranced or flavored orthodontic appliances and a method of forming such appliances where the flavor or fragrance endures longer than 2 to 3 days, the preparation technique is the traditional "cold cure" process and it can be applied to most all orthodontic appliances. The terms fragranced oils or flavored oils are used interchangeably or separately depending upon their intended function. In the case of orthodontic appliances, both functions are useful or important. As will be understood, however, a fragranced oil such as spearmint also has a flavor. For ease of description herein, the term fragrance and fragranced oil will be used to include either or both functions regardless of whether the primary purpose of the additive is for flavoring or fragrance.

The above mentioned objectives are attained by the present invention which is directed to a fragranced orthodontic appliance which provides for a flavor and fragrance that endures significantly longer than 2 to 3 days.

The present invention is directed to a cold cure fragranced acrylic orthodontic appliance comprised of a hard cold cure base member that is prepared from a suitable powdered polymeric component and a liquid monomeric component, wherein both the liquid and the powdered component contain a selected fragrancing oil. Further, the suitable powdered polymeric component is comprised of one or more monomeric derivatives of acrylic or preferably methacrylic acid and a fragrancing oil. These materials are designed such that once the liquid monomeric component and the polymeric powdered component are combined under the appropriate conditions the material will "cold cure" and result in a homogeneous acrylic copolymer having a longer lasting fragrance.

The method of producing the fragranced orthodontic appliance of this invention utilizes suspension polymerization to encapsulate the fragrance in the powdered component thereby permitting inclusion of the fragrance in both the liquid and powder components of the appliance. The method of this invention thus includes forming a polymerized powder containing the desired fragrance by mixing a monomer or more preferably comonomers and a fragrance oil in a water suspension, heating and agitating the suspension to initiate suspension polymerization, separating and drying the polymerized polymer as small spheres or beads of the polymer containing the fragrance. The liquid component is formed by mixing the acrylic monomer or preferably methacrylate comonomers with a flavoring agent. Finally, the fragranced polymeric orthodontic appliance is formed by applying the polymeric powder component and liquid component to a mold of an orthodontic appliance and cold curing the orthodontic appliance under pressure by conventional means.

In the most preferred embodiments of the fragranced orthodontic appliance and method of this invention, the monomers are of derivatives of acrylic acid, more preferably derivatives of methacrylic acid, most preferably methyl methacrylic acid or ester. Thus, the method of this invention includes forming the polymeric powder component by mixing an acrylic monomer or more preferably a monomer of methacrylate, most preferably derivatives of methyl methacrylate acid and a fragrance oil in a water suspension forming a methacrylate or acrylic acid ester, then heating and agitating the suspension to initiate the polymerization and drying the acrylic or methacrylate polymer or copolymer to form a powder having the preferred fragrance encapsulated therein. The liquid component also preferably includes a monomer or comonomer selected from the group consisting of methacrylic or acrylic acid, more preferably methacrylic acid esters, most preferably including at least 30% by weight methyl methacrylate or more preferably at least 50% methyl methacrylate. The comonomer is preferably butyl methacrylate. The method of forming the liquid component thus includes mixing the monomer and comonomer preferably including methacrylic acid esters, most preferably including methyl methacrylate and a fragrance oil. The orthodontic appliance is then made by applying the polymeric fragranced powder and the liquid fragranced component to a mold of the orthodontic appliance and cold curing the orthodontic appliance as described.

DETAILED DESCRIPTION OF THE PREFERRED EMBODIMENTS

The present invention relates to the preparation of fragranced orthodontic appliances using what is known in the art as "cold cure" acrylic. The cold cure acrylic is comprised of a fragranced powdered polymeric component and a fragranced liquid monomeric component that once combined together to solidify into a homogeneous acrylic copolymer member. This acrylic member can optionally consist of wires and auxiliary devices imbedded into the hard acrylic resin.

Although not wishing to be bound to any single theory as to why the fragrance in the appliance is longer lasting, it is the belief of the inventors that the fragranced orthodontic appliances provide for an enduring flavor through a combination of principles. The first principle is that the acrylic composition should contain sufficient quantity of fragrance such that the patient experiences the desired intensity of this flavor or fragrance. Adding fragrancing oil to both the liquid and the powdered components of the cold cure resin allows the addition of sufficiently high levels of fragrance or flavor without inhibiting the "cold cure" performance as reported in the prior art. The second principle is that a mechanism for entrapping the fragrancing oil to be released over a sufficiently long period is required. Reduction of the glass transition temperature of the acrylic polymer by a combination of adding the fragrance and the use of comonomers results in an acrylic polymer hard enough to function as an orthodontic appliance yet the glass transition temperature is sufficiently depressed to provide a mechanism for release. The combination of these two principles shows significant improvements in the duration of the fragrance.

The fragranced powdered polymeric component is preferably comprised of a fragrance, one or more monomeric derivatives of acrylic or methacrylic acid, and conventional additives, such that the resulting acrylic member is sufficiently hard to be used as an orthodontic appliance while the glass transition temperature is reduced below that of poly (methyl methacrylate), for example, such that the entrapped flavor has a mechanism to be released. Additives consist of peroxides useful in the promotion of free radical polymerization suspension polymerization.

Suspension polymerization is a commonly used process to polymerize water insoluble monomers using water as the reaction medium. In this method, a water insoluble monomer or a mixture of monomers is dispersed by strong mechanical agitation into droplets suspended in an aqueous liquid phase. The monomer droplets are then polymerized while dispersion is maintained by continuous agitation. Dispersing agents such as partially hydrolyzed poly(vinyl alcohol) and/or surfactants are typically added to the water that inhibits the coagulation of the dispersed droplets during polymerization. Polymerization initiators that are soluble in the monomer phase are generally used. Small spheres or beads are formed during the polymerization, the size being depending on the conditions used in the polymerization. For the purposes of the orthodontic appliances of this invention, the small beads are small enough to be considered a powder.

The fragrance oil is a material or materials that preferably have been certified and approved by the United States Food and Drug Administration. Below is a brief list, by way of example only, of suitable fragrance oils that can be used in the present method.

Bubblemint SR#014665

Spearmint SR#015925

These materials are available from the Flavors of North America, Inc. The preferred amount of the fragrance oil, commonly referred to as a flavoring oil, in the polymer can vary depending on the composition of the oil, which governs the particular flavor desired. Each oil may require a slightly different optimal level to achieve the desired effect and experimentation is the only method that can determine the exact quantity of oil in the powdered polymer is from 1% to 35% by weight with 5% to 30% being more preferred and 10% to 25% being most preferred. All percentages defined herein are in weight percentage.

The preferred monomeric derivatives of methacrylic or acrylic acid can be acids, esters, di-esters, amides, di-amides, hydroxy esters, amino esters, hydroxy amides, amino amides, etc. The more preferred derivatives of acrylic acid are esters of methacrylic acid. Acrylic acid is used as a monomer for polyacrylic and polymethacrylic acids and other acrylic polymers and, as used herein, is generic to this family of acids and esters including for example methacrylic acid and esters thereof. The esters can be derived from 1 carbon to 32 carbon hydroxyl functional materials. Typical examples include methyl, ethyl, n-propyl, iso-propyl, n-butyl, iso-butyl, tert-butyl, pentyl, hexyl, 2-ethyl hexyl, 2-hydroxy ethyl, glycerol, stearyl, etc. More preferably the esters are derived from primary alcohols with 1 to 8 carbons and most preferably primary alcohols with 1 to 4 carbons, i.e., methyl, ethyl, propyl, and butyl esters.

The polymeric powder is preferably comprised of 1 and may be as many as 10 methacrylic esters. More preferably it is comprised of at least 2 and as many as 5 methacrylic esters and, most preferably at least 2 and as many as 3. The exact combination of the methacrylic ester monomers that produces a polymer with the desired glass transition temperature depends on the fragrancing oil and its interaction with the copolymer produced from this combination of methacrylic esters. The preferred combination of methacrylic acid esters in the copolymer is comprised of 30% to 99% menthyl methacrylate and from 1% to 70% of the comonomers. More preferred is from 55% to 95% methyl methacrylate and from 5% to 45% comonomers. Most preferred is from 70% to 90% methyl methacrylate and 10% to 30% comonomers. The most preferred comonomer is butyl methacrylate.

The fragranced liquid monomeric component is comprised of a fragrance, at least two derivatives of acrylic or methacrylic acid, and additives such when the liquid is admixed with the powdered polymeric component that the resilient acrylic member is sufficiently hard to be used as an orthodontic appliance while the glass transition temperature is reduced below that of poly(methyl methacrylate) such that the entrapped or encapsulated fragrance has a mechanism to be released. Additives consist of amines useful in promotion of free radical polymerization, surfactants, dyes, colorants, placticizers, fillers, pigments, etc.

The fragrance oil is material or materials that have preferably been certified and approved by the United States Food and Drug Administration and have been listed previously. The preferred amount of the fragrance oil in the polymer can vary depending on the composition of the oil, which governs the particular fragrance or flavor desired. Each oil may require a slightly different optimal level to achieve the desired effect and experimentation is the only method that can determine the exact quantity of oil required. The preferred range for the level of fragrancing oil in the monomeric liquid is form 1% to 35% by weight with 5% to 30% being more preferred and 10% to 25% being most preferred.

The monomeric derivatives of methacrylic or acrylic acid can be acids, esters, di-esters, amides, di-amides, hydroxy esters, amino esters, amino esters, hydroxy amides, amino amides, etc. The preferred derivatives of methacrylic or acrylic acid are esters of methacrylic acid. The esters can be derived from 1 carbon to 32 carbon hydroxyl functional materials. Typical examples include methyl, ethyl, n-propyl, iso-propyl, n-butyl, iso-butyl, tert-butyl, pentyl, hexyl, 2-ethyl hexyl, 2-hydroxy ethyl, glycerol, steryl, etc. More preferably the esters are derived from primary alcohols with 1 to 4 carbons, i.e, methyl, ethyl, propyl, and butyl esters.

The monomeric liquid is preferably comprised of at least 2 and as many as 20 methacrylic esters. More preferred are at least 2 and as many as 7 and, most preferred is at least 2 and as many as 4. The exact combination of the methacrylic ester monomers that produces a polymer with the desired glass transition temperature depends on the fragrancing oil and its interaction with the copolymer produced from this combination of methacrylic esters. The preferred combination of methacrylic esters. The preferred combination of methacrylic acid esters is comprised of 30% to 99% methacrylate and from 1% to 70% of comonomers. More preferred is from 50% to 95% methyl methacrylate and from 5% to 50% comonomers. Most preferred is from 65% to 90% methyl methacrylate and 10% to 35% comonomers.

Other conventional additives generally used in the art may also be used in the present invention. Examples include reflective sparkles, decals, pigments or other decorative materials.

The improved fragrance orthodontic appliance of this invention is then formed by conventional cold curing techniques. That is, the fragranced liquid momomeric component and fragranced powdered polymeric component are combined together over a configured custom mold by conventional cold cure methods, wherein the appliance is molded at a temperature of about 110° F. and a pressure of about 25 psi. Because the cold cure method will vary with the manufacturer of the appliances, the percentages of the liquid monomeric component and powdered polymeric component will vary depending upon the technique used to mold the appliance. However, in a typical application, the ratio of the fragranced liquid monomeric component to the fragranced powdered polymeric component will be about 1 to 2 or about 33% of the liquid monomeric component and 66% of the powdered polymeric component. Thus, the preferred embodiment of the fragranced orthodontic appliance of this invention will comprise 30% to 99% polymethacrylates or polyacrylics and 1% to 35% fragrance oil, wherein the more preferred embodiment comprises 55% to 95% methyl methacrylate and 5% to 50% comononers, most preferably including butyl methacrylate and 5% to 30% fragrance oil. Most preferably, the fragranced orthodontic appliance of this invention comprises 65% to 95% methyl methacrylate and 10% to 35% comonomers preferably comprising or including butyl methacrylate and 10% to 25% fragrance. Because the fragrance is included in both the liquid monomeric component and the powdered polymeric component, the fragrance oil is thus encapsulated within the polymeric preferably polymethacrylate substrate and substantially evenly distributed therethrough.

The method of forming the fragranced orthodontic appliance of this invention generally includes mixing the preferred monomer or comonomer and the fragrance oil in a water suspension and forming the polymeric powder component by suspension polymerization, mixing the preferred monomer or comonomer and a fragrance oil to form the liquid component and applying the polymeric powder component and liquid component to a mold of an orthodontic appliance and cold curing the orthodontic appliance as described. As will be understood by those skilled in suspension polymerization, the polymer powder component may be formed by dissolving a surfactant such as polyvinyl alcohol in water, then adding the selected monomers and the fragrance oil to the water to form a water suspension. The suspension is then agitated and heated to a temperature sufficient to cause the exothermic reaction of polymerization which generally occurs at about 80° F. to 85° F. for polymerization of polymethacrylates. After the exothermic polymerization reaction is complete in about one to two hours, the suspension is spun, cooled and filtered. The wet polymer is then dried forming beads or spheres of fragranced polymeric powder. The liquid component is formed by mixing the components thereof which include the preferred monomer, preferably acrylic acid or more preferably methacrylic acid and the fragrance oil. In a typical application, the liquid component also includes a crosslinker such as ethylene glycol dimethacrylate and an initiator, such as amine accelerator at generally about 2% each. The most preferred liquid component includes methyl methacrylic acid or ester and butyl methacrylic acid or ester at a ratio of about 5 to 1 methyl methacrylic acid.

EXAMPLES

The following examples demonstrate the flavor or fragrance properties of the present invention. Sample retainers were prepared using conventional techniques. A mixture of the powdered polymeric component and liquid monomeric component were applied to a plaster orthodontic model. The weight ratio of the components was approximately 67% powder to 33% liquid or a ratio of about 2 to 1. The ratio will however vary depending upon the technique used by the manufacturer by as much as 10%. The model holding the mixture was then place in an industry standard pressure pot controlled to 120° F. and then 20 p.s.i. of air pressure applied. The retainers were removed from the pot after 20 minutes and allowed to cool on the model. The retainers were then removed from the model, ground and polished to a finished retainer each specimen weighing approximately 5 grams.

The compositions of the powdered polymeric components employed are listed in Table 1. The compositions of the liquid monomeric components employed are listed in Table 2. For simplicity in analyzing the data a nomenclature has been adopted that describes the composition of each component. The first two digits describe the ratio of the monomeric species, MMA/BMA (methyl methacrylate/butyl methacrylate) and the third digit describes the total quantity of flavor in the mixture. To simplify the discussion for the powdered polymeric component the BPO is ignored. For example, the powdered polymeric component listed as P1 in Table 1 is described as (85/15/15). This powdered polymer is comprised of 15% flavor and the balance of the material has a monomer ratio of 85/15 MMA/BMA. To simplify the discussion for the liquid monomeric component the EGDMA is treated as MMA and the amine ignored. For example, the liquid monomeric component listed as L4 in Table 2 is described as (90/10/10). This liquid mixture contains 10% flavor and the balance of the mixture has a monomer ratio of 90/10 MMA/BMA.

TABLE 1

Powdered Polymer Component Compositions

|  | P1 (85/15/15) | P2 (90/10/15) | P3 (85/15/10) | P4 (90/10/10) | P5 (85/15/15) |
|---|---|---|---|---|---|
| MMA | 71.4 | 75.6 | 75.6 | 80.1 | 72.2 |
| BMA | 12.6 | 8.4 | 13.4 | 8.9 | 12.8 |
| Flavor | 15 | 15 | 10 | 10 | 15 |
| BPO | 1 | 1 | 1 | 1 | 1 |

TABLE 2

Liquid Monomeric Component Compositions

|  | L1 (85/15/15) | L2 (90/10/15) | L3 (85/15/10) | L4 (90/10/10) |
|---|---|---|---|---|
| MMA | 68.9 | 72.9 | 73.1 | 77.4 |
| BMA | 12.1 | 8.1 | 12.9 | 8.6 |
| EGDMA | 2 | 2 | 2 | 2 |
| Amine | 2 | 2 | 2 | 2 |
| Flavor | 15 | 15 | 10 | 10 |

MMA is methyl methacrylate available from Aldrich Chemical.
BMA is n-butyl methacrylate available from Aldrich Chemical.
EGDMA is ethylene glycol di-methacrylate available from Aldrich Chemical.
Amine is N,N-Dimethyl-p-toluidine available from Aldrich Chemical.
BPO is benzoyl peroxide available from Aldrich Chemical.
Flavor is bubblemint available from Flavors of North America, Inc.

The powdered polymer component is formed by conventional suspension polymerization techniques, except that the polymeric powder includes a fragrancing oil which reduces the glass transistion temperature of the methacrylates as described above. In a typical application, the methyl methacrylate and the butyl methacrylate are first dissolved in benzol peroxide which acts as an initiator and the fragrance oil is then added. In one example, 81 grams of methyl methacrylate and 9 grams of butyl methacrylate were dissolved in 1 gram of benzol peroxide. Next, the water suspension was prepared by adding polyvinyl alcohol (87% to 89% hydrolyzed) to water and the water was heated to near boiling to dissolve the polyvinyl alcohol. In this example, 20 grams of polyvinyl alcohol were added to 400 grams (2 liters) of water. The water and polyvinyl alcohol were then added to a reaction vessel which included a shear mixture and a heater. The methyl methacrylate and butyl methacrylate were then added to the water and the reaction vessel was agitated by a conventional small turban blade and a cuff heater. The suspension was then heated to the exothermic reaction temperature of the methacrylates, which occurred between about 85° C. and 87° C. The exothermic reaction occurred after about one hour and continued for three to four hours. The reaction vessel was then cooled and the polymethacrylate and fragrance oil was then filtered from the water and air dried in a fume eliminator for two to three days. Finally, the polymer was sifted for fineness.

As set forth above, the liquid monomer component may be prepared by mixing the components. In a typical example, the components includes 77.4 grams of methyl methacrylate, 8.6 grams of butyl methacrylate, 10 grams of the fragrance oil, 2 grams of ethylene glycol diemethacrylate which acts a crosslinker and 2 grams of an amine accelerator. The powdered polymer component and the liquid monomer or comonomer component are then combined and molded into the fragranced orthodontic appliance of this invention as described herein.

The retainers once prepared were all found to have a strong fragrance. The fragrance was recorded according to a rating scale of 1 to 5 with 5 being strong and 1 being difficult to detect. The retainers were left at room temperature for a period of 4 weeks and the fragrance rated again. The results of this test and an estimate of the retainers composition can be found in Table 3. Clearly it can be found that the higher the total quantity of flavor the longer the flavor or fragrance will last. Further, it was found that the higher the quantity of comonomer the longer the flavor lasted and the combination of high levels of comonomer and flavor lasted the longest. A more subtle observation is that the polymeric powder component had a dominant effect on the results.

TABLE 3

Retainer Composition and Fragrance Longevity After 28 Days

| Powdered Component | P1 (85/15/15) | | P2 (90/10/15) | | P3 (85/15/10) | | P4 (90/10/10) | |
|---|---|---|---|---|---|---|---|---|
| | Retainer Composition MMA/BMA/Fla. | Performance | Retainer Composition MMA/BMA/Fla. | Performance | Retainer Composition MMA/BMA/Fla. | Performance | Retainer Composition MMA/BMA/Fla. | Performance |
| Liquid Component | | | | | | | | |
| L1 (85/15/15) | 72.3/12.7/15 | 5 | 75.1/9.9/15 | 3 | 75.1/13.2/11.7 | 2 | 78.1/10.2/11.7 | 2 |
| L2 (90/10/15) | 73.7/11.3/15 | 5 | 76.5/8.5/15 | 3 | 76.5/11.8/11.7 | 3 | 79.5/8.8/11.7 | 2 |

TABLE 3-continued

Retainer Composition and Fragrance Longevity After 28 Days

| | P1 (85/15/15) | | P2 (90/10/15) | | P3 (85/15/10) | | P4 (90/10/10) | |
|---|---|---|---|---|---|---|---|---|
| Powdered Component | Retainer Composition MMA/BMA/Fla. | Performance | Retainer Composition MMA/BMA/Fla. | Performance | Retainer Composition MMA/BMA/Fla. | Performance | Retainer Composition MMA/BMA/Fla. | Performance |
| L3 (85/15/10) | 73.7/13/13.3 | 4 | 76.5/10.2/13.3 | 3 | 76.5/13.5/10 | 1 | 79.5/10.5/10 | 1 |
| L4 (90/10/10) | 75.2/11.5/13.3 | 5 | 78/8.7/13.3 | 2 | 78/12/10 | 1 | 81/9/10 | 1 |

Performance Ratings:
5 = strong fragrance,
1 = difficult to detect fragrance

Comparative examples of flavor in combination with MMA without a comonomer were prepared. Table 4 describes the experiments and approximates the total composition of the retainer based on the assumption of 67% powder to 33% liquid. Within these comparative examples the compositions described in U.S. Pat. No. 5,080,583 has been included. Similar to the previous examples the comparative examples were rated from 1 to 5 initially and after a period of 28 days. The initial ratings were high but after even a few days the fragrance had disappeared altogether. The ratings that are found in Table 4 were recorded after 28 days. Essentially no flavor could be detected.

TABLE 4

Comparative Examples

| | Powder Component | Retainer Composition MMA/BMA/Fla. | Performance | Retainer Composition MMA/BMA/Fla. | Performance |
|---|---|---|---|---|---|
| | | 100/0/0 | | 100/0/10 | |
| Liquid | 100/0/0 | 100/0/0 | 0 | 100/0/6. | 0 |
| | 100/0/10 | 100/0/3.3 | 0 | 100/0/10 | 0 |

From the comparative examples it is observed that the application of the principle of adding flavor to the liquid alone does not result in a flavor or fragrance that endures. Further, the application of the principle of increasing the flavor or fragrance without inhibiting the cold cure. i.e., including flavor in the polymeric powder, does not result in a flavor that endures. It is found that only through a combination of the principles of a sufficiently high level of flavor and the use of a comonomer that suppresses the glass transition temperature of the poly(methyl methacrylate) thus providing a mechanism for the flavor to escape.

What is claimed is:

1. A method of forming a fragranced polymeric orthodontic appliance comprising the following steps:

mixing a monomer and a fragrance oil in a water suspension, heating and agitating said suspension thereby forming a polymeric powder containing said fragrance oil by suspension polymerization;

mixing a monomer and a fragrance oil forming a liquid component; and applying said polymeric powder and liquid component to a mold of an orthodontic appliance and cold curing said orthodontic appliance.

2. The method of forming a fragranced polymeric orthodontic appliance as defined in claim 1, wherein said step of forming said polymeric powder is further defined by mixing a monomer of methacrylic or acrylic acid with a fragrance oil in a water suspension thereby forming a methacrylic or acrylic ester, heating and agitating said suspension thereby forming a polymethacrylate or polyacrylic powder comprising said fragrance oil.

3. The method of forming a fragranced polymeric orthodontic appliance as defined in claim 2, wherein said step of forming said polymeric powder is further defined by mixing at least two monomers of methacrylic acid with a fragrance oil in a water suspension, heating and agitating said suspension to form a polymethacrylate resin containing said fragrance oil by suspension polymerization.

4. The method of forming a fragranced polymeric orthodontic appliance as defined in claim 3, wherein said step of forming said polymeric powder is further defined by mixing methyl methacrylic acid with at least one of said monomers of methacrylic acid and a fragrance oil in a water suspension.

5. The method of forming a fragranced polymeric orthodontic appliance as defined in claim 3, wherein said step of forming said polymeric powder is further defined by said monomers of methacrylic acid including 30% to 99% by weight percent of methyl methacrylate and 1% to 70% by weight percent of comonomers.

6. The method of forming a fragranced polymeric orthodontic appliance as defined in claim 5, wherein said step of mixing said monomer and said fragrance oil to form said polymeric powder is further defined by mixing 1% to 35% by weight percent of said fragrance oil with total weight percent of said monomers of methacrylic acid.

7. The method of forming a fragranced polymeric orthodontic appliance as defined in claim 3, wherein said step of forming polymeric powder is further defined by forming a mixture of at least two monomers of methacrylic acid and a fragrance oil, wherein said mixture includes 55% to 95% by weight percent of methyl methacrylate, 5% to 45% by weight percent of comonomers and 5% to 30% by weight percent of said fragrance oil.

* * * * *